United States Patent
Pitts et al.

(10) Patent No.: US 10,357,337 B2
(45) Date of Patent: Jul. 23, 2019

(54) ORTHODONTIC SYSTEM WITH VARIABLY-SIZED ARCHWIRE SLOT

(71) Applicant: World Class Technology Corporation, McMinnville, OR (US)

(72) Inventors: Thomas Pitts, Reno, NV (US); Alberto Ruiz-Vela, Rancho Cucamonga, CA (US)

(73) Assignee: World Class Technology Corporation, McMinnville, OR (US)

( * ) Notice: Subject to any disclaimer, the term of this patent is extended or adjusted under 35 U.S.C. 154(b) by 100 days.

(21) Appl. No.: 15/601,646

(22) Filed: May 22, 2017

(65) Prior Publication Data
US 2018/0185121 A1  Jul. 5, 2018

Related U.S. Application Data

(60) Provisional application No. 62/441,839, filed on Jan. 3, 2017.

(51) Int. Cl.
*A61C 7/12* (2006.01)
*A61C 7/20* (2006.01)

(52) U.S. Cl.
CPC . *A61C 7/12* (2013.01); *A61C 7/20* (2013.01)

(58) Field of Classification Search
CPC .... A61C 7/00; A61C 7/12; A61C 7/14; A61C 7/141
USPC ...................................... 433/2–22
See application file for complete search history.

(56) References Cited

U.S. PATENT DOCUMENTS

| | | | | |
|---|---|---|---|---|
| 2,908,974 A | * | 10/1959 | Stifter | A61C 7/12 433/16 |
| 3,660,900 A | * | 5/1972 | Andrews | A61C 7/12 433/16 |
| 3,916,526 A | | 11/1975 | Schudy | |
| 4,597,739 A | * | 7/1986 | Rosenberg | A61C 7/14 433/16 |
| 5,044,945 A | * | 9/1991 | Peterson | A61C 7/12 433/8 |
| 5,540,586 A | * | 7/1996 | Hanson | A61C 7/20 433/11 |
| 2002/0110775 A1 | * | 8/2002 | Abels | A61C 7/125 433/11 |
| 2003/0163291 A1 | | 8/2003 | Jordan et al. | |
| 2005/0244774 A1 | | 11/2005 | Abels et al. | |
| 2006/0147872 A1 | * | 7/2006 | Andreiko | A61C 7/00 433/24 |
| 2007/0092849 A1 | | 4/2007 | Cosse | |
| 2009/0136889 A1 | | 5/2009 | Abels et al. | |
| 2010/0323315 A1 | | 12/2010 | Takemoto | |
| 2011/0151390 A1 | | 6/2011 | Takemoto | |
| 2011/0183280 A1 | * | 7/2011 | Cosse | A61C 7/14 433/13 |

(Continued)

OTHER PUBLICATIONS

International Searching Authority United States Patent Office, International Search Report and Written Opinion, PCT/US18/12085, dated Mar. 9, 2018, 11 pp.

(Continued)

*Primary Examiner* — Wade Miles
*Assistant Examiner* — Matthew P Saunders
(74) *Attorney, Agent, or Firm* — Stoel Rives LLP

(57) ABSTRACT

An orthodontic system having brackets with variably sized slots.

15 Claims, 6 Drawing Sheets

(56) References Cited

U.S. PATENT DOCUMENTS

| | | | |
|---|---|---|---|
| 2012/0094247 A1* | 4/2012 | Lewis | A61C 7/14 |
| | | | 433/9 |
| 2012/0308952 A1* | 12/2012 | Cosse | A61C 7/12 |
| | | | 433/3 |
| 2013/0252194 A1 | 9/2013 | Hagelganz et al. | |
| 2015/0050612 A1 | 2/2015 | Damon et al. | |
| 2017/0172708 A1 | 6/2017 | Damon et al. | |

OTHER PUBLICATIONS

International Search Report and Written Opinion for International Application No. PCT/US2018/028680, dated Jul. 11, 2018, 9 pages.

\* cited by examiner

US 10,357,337 B2

ORTHODONTIC SYSTEM WITH VARIABLY-SIZED ARCHWIRE SLOT

CROSS-REFERENCE TO RELATED APPLICATIONS

This application is related to and claims priority from U.S. Provisional Application Ser. No. 62/441,839 filed Jan. 3, 2017.

BACKGROUND

This disclosure relates to orthodontic appliances, and more particularly to orthodontic appliances used to correct misalignment of a patient's teeth. Such appliances, typically referred to as braces, are used to align and straighten teeth so as to both position them with regard to a person's bite, as well as improve the appearance of a patient's mouth. Such appliances may be used to correct underbites, overbites, malocclusions, and various other misalignments of the teeth.

Braces usually include three types of structures assembled over a patient's teeth. First, to each tooth undergoing treatment is attached a bracket having a slot. Attachment is usually accomplished using some form of adhesive. An archwire is then inserted and tightened into the slots of adjacent brackets of the applicable upper/lower row of teeth. The archwire is held in place in the respective slots by some form of ligating structure. Historically, these ligating structures were elastic bands, but a more recent alternative employs a self-ligating structure of the bracket that uses sliding or hinged doors that alternatively open the slots in the brackets to insert an archwire, and close the slot to retain the archwire in place within the slot. Once this assembly is in place, the tension of the archwire will, over time, align the patient's teeth toward a desired position.

Treatment of a patient's teeth using braces requires several repeated appointments to monitor progress and make adjustments to the braces as treatment progresses. The length of the treatment, and the repeated adjustments is often an annoyance to the patient. What is desired, therefore, is an improved system for treating a patient with braces that reduces the length of treatment by more efficiently aligning a patient's teeth.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION

Preliminarily, the following terms will be accorded the meanings that respectively follow them, which should be understood by those familiar with the art. These meanings are provided to facilitate understanding of the specification by those unskilled in the art, as well.

Anterior the direction towards the front of the head, or the lips; opposite of "posterior."

Anterior teeth—the teeth on either one of the mandibular or maxillary jaws extending from one canine tooth to the other canine tooth.

Buccal—the direction towards the cheek, typically used in connection with posterior teeth; opposite of "lingual."

Buccal-lingual direction—a direction through or along any particular posterior tooth extending between a patient's cheek and the patient's tongue.

Distal—the direction on the side of a particular tooth away from the dental midline; opposite of mesial.

Dental arch—a row of teeth in either of the mandibular or maxillary jaws.

Dental midline—an imaginary line dividing a patient's mouth into two halves, extending through the patients two middle anterior teeth and towards the back of the mouth.

Gingival—a direction towards the gums beneath a particular tooth.

Incisal—a direction towards the biting surface of a particular anterior tooth.

Incisal-gingival direction—a direction through or along any particular anterior tooth extending from the biting surface to the gums beneath that tooth.

Labial—the direction towards the lips, typically used in connection with anterior teeth; opposite of lingual.

Labial-lingual direction—a direction through or along any particular anterior tooth extending between the patient's lips to the patient's tongue.

Mandibular—related to the lower jaw.

Maxillary—related to the upper jaw.

Mesial—the direction on the side of a particular tooth toward the dental midline; opposite of distal.

Mesial-distal direction—the direction through any particular tooth extending from the mesial side of the tooth to the distal side of the tooth. The mesial-distal direction, relative to a tooth, is essentially along the curved line through the relevant upper or lower row of teeth.

Occlusial—a direction towards the biting surface of a particular posterior tooth.

Occlusal-gingival direction—a direction through or along any particular posterior tooth extending from the biting surface to the gums beneath that tooth Posterior—the direction towards the back of the head; opposite of anterior.

Posterior teeth—the teeth on either one of the mandibular or maxillary jaws posterior of a canine tooth.

Rotation—angular rotation of a tooth during the course of treatment around a vertical axis oriented in the incisal-gingival direction.

Tip—angular rotation of a tooth during the course of treatment around a horizontal axis oriented in the buccal-lingual direction.

Torque—angular rotation of a tooth during the course of treatment around a horizontal axis oriented in the mesial-distal direction.

Figure 1:
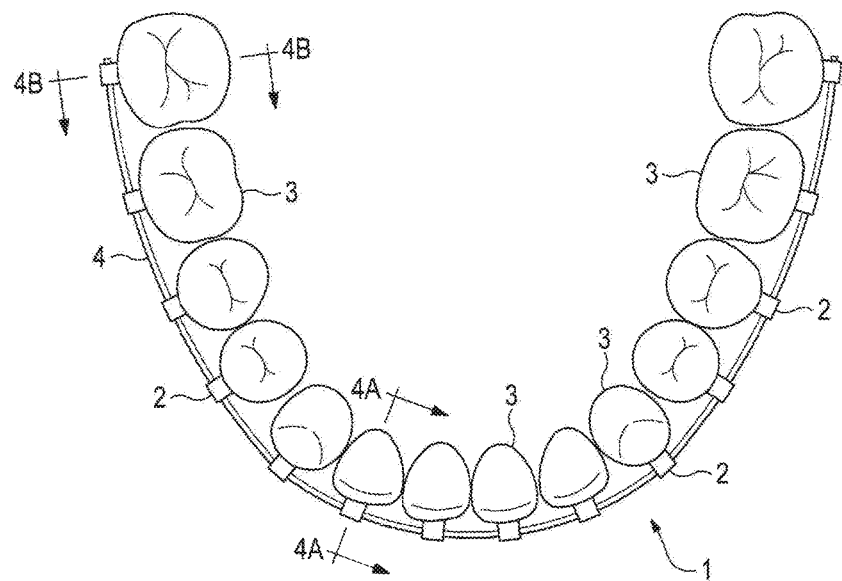
FIG. 1 shows a row of teeth with dental appliances attached thereto using an archwire.
Figure 2:
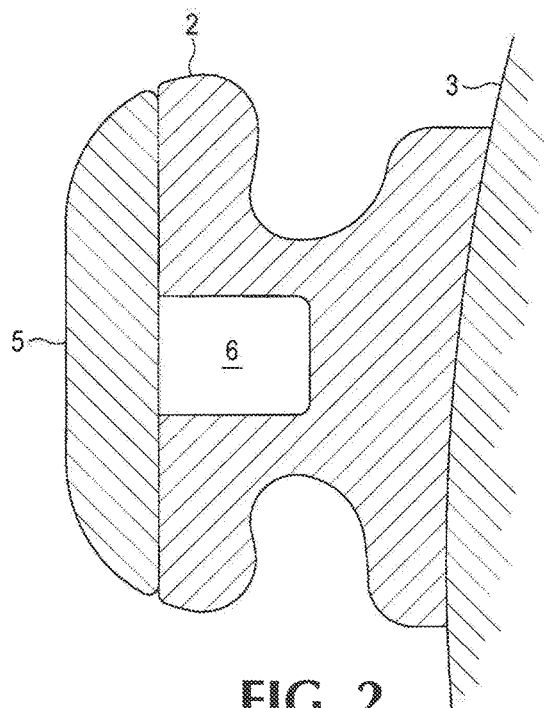
FIG. 2 shows a sectional view of a dental appliance of FIG. 1.

Referring to FIGS. 1 and 2, a treatment system 1 comprising braces may be applied to a row of patient's teeth 3 using a plurality of brackets 2 connected together by an archwire 4 through appropriate means such as an archwire slot 6, and a ligating structure such as a cover 5 for the archwire slot 6. As noted earlier, treatment of a patient using braces typically requires repeated adjustment of the archwire 4 so that, over time, the tension in the archwire 4, applied to the teeth 3 through the brackets 2, causes the teeth 3 to migrate to a desired final position.

Figure 3A:
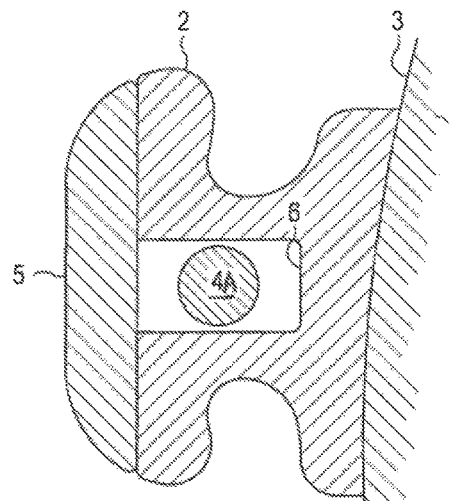
FIGS. 3A-3C illustrate the temporal progression of a treatment program that progressively applies differently-shaped archwires to the dental appliances of FIG. 1 so as to incrementally move a patient's teeth towards a desired position.
Figure 3B:
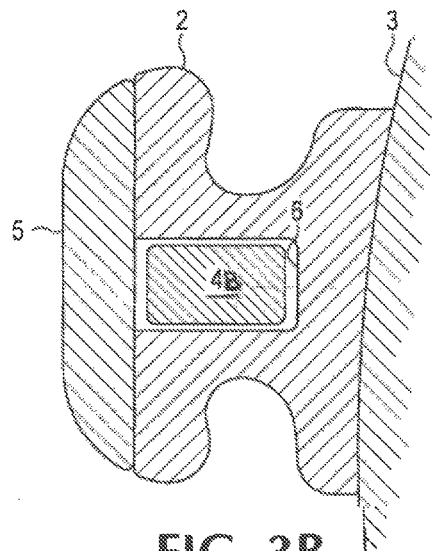
Figure 3C:
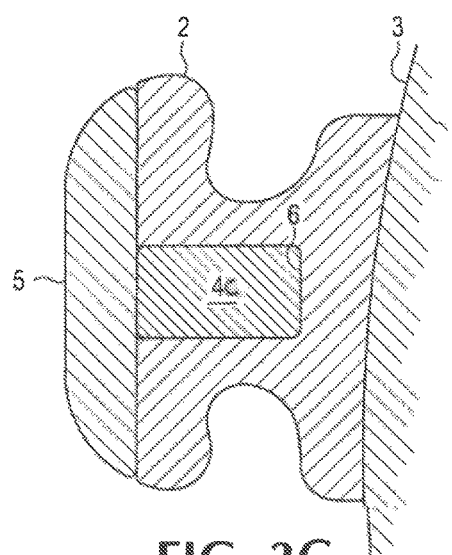

FIGS. 3A, 3B, and 3C collectively illustrate a common prior art adjustment procedure. Referring to FIG. 3A, an archwire slot 6 in the respective brackets 2 adhered to each of a patent's teeth 3 along a dental arch may be formed as an elongated rectangular aperture closed at one end by a ligating structure 5. The ligating structure 5 may be a sliding or hinged door over the archwire slot 6, or may be an elastic band, or any other appropriate structure. When a set of braces is first applied to each of a patient's teeth, an archwire 4A of a circular cross section may be used. Usually the circular archwire 4A is made of a nickel-titanium material that is relatively flexible so that, in combination with the circular cross-sectioned archwire 4A fitted in a rectangular slot 6, the archwire 4A applies relatively low forces to a patient's teeth 3, and the brackets 2 have significant play to move relative to each other as the teeth 3 move towards a more aligned state. Furthermore, when a circular archwire 4A is used, there is no torque control of the teeth 3 since twisting the archwire 4A will not apply any rotational forces to the bracket 2.

Eventually, in another stage of treatment shown in FIG. 3B, the archwire 4A of a circular cross section is replaced by an archwire 4B of a rectangular square cross section that is smaller than the archwire slot 6, which can also be made of nickel titanium, but is sometimes made of a beta-titanium alloy, stiffer than the nickel-titanium circular archwire 4A it replaces. This second stage of treatment steps up the force and control applied to the teeth 3 through the archwire 4B and brackets 2, and the brackets 2 have less play relative to the archwire 4A than existed in the first stage of treatment.

Finally, in a third, final stage of treatment shown in FIG. 3C, the archwire 4B of a small rectangular cross section is replaced by an archwire 4C of a larger rectangular cross section, which is typically made of stainless steel, stiffer than the nickel-titanium square archwire 4B it replaces. This third stage of treatment again steps up the force and control applied to the teeth 3 through the archwire 4C and brackets 2, and the brackets 2 have very little play relative to each other than existed in the first and second stages of treatment given the material of the archwire 4C and the fact that the cross section of the archwire 4L is shaped to closely fit within the archwire slot 6.

The present inventors discovered that a more efficient treatment system could be applied than that shown in FIGS. 3A-3C, based on the realization that not all teeth need to be simultaneously subjected to the same amount of play during treatment. Specifically, the present inventors realized that one of the primary objects of dental treatment with braces is the precise positioning of the anterior teeth so as to achieve a desired aesthetic look, and that positioning of the posterior teeth need not be as precise. Accordingly, an improved system preferably uses a set of brackets 2 for placement along a dental arch, either mandibular or maxillary, where the cross section of the archwire slot varies in the distal direction of the arch from the dental midline, i.e. from the anterior brackets to the posterior brackets. This system provides for the following benefits compared to current systems:

Improved quality of treatment due to increase control of the teeth in the anterior segment of the dental arch.

Earlier control of tooth movement in treatment, resulting in a reduced treatment time when compared to current systems while providing appropriate freedom of movement such that the teeth can efficiently move to the desired position.

An improved patient experience due to low and efficient forces due to appropriate sizing of the archwire dimensions.

Figure 4A:
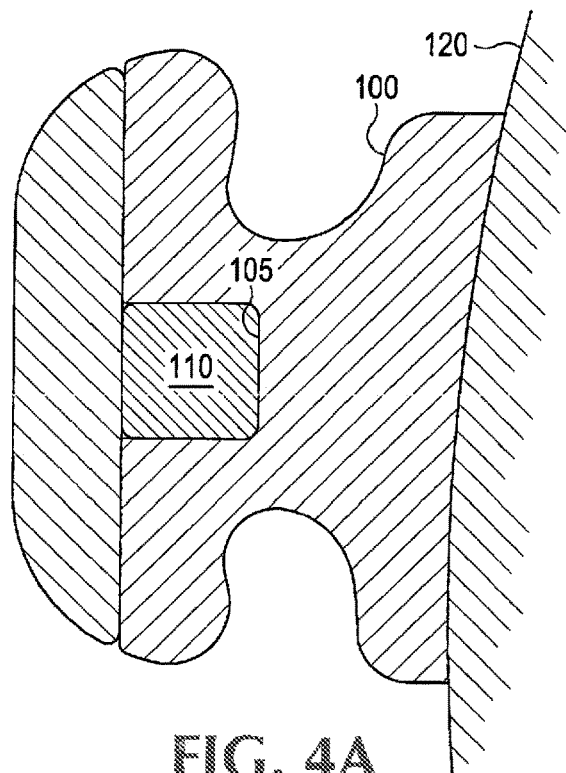
FIG. 4A shows a cross section along line A-A of FIG. 1 using a novel orthodontic system disclosed in the present specification.

In the improved system, the archwire slots of respective brackets are sized proportionally to both the size of the archwire to be inserted in the final stage of treatment, as well as the position of the tooth to which the bracket forming the archwire slot is to be affixed along the mesial-distal direction of the dental arch. FIG. 4A, for example, shows an improved dental bracket 100 having a square archwire slot 105 sized to closely fit around an archwire 110 to be used in the final stage of treatment. The dental bracket having archwire slot 100 is preferably attached to an anterior tooth 120 positioned along the line A-A of FIG. 1. Preferably, the brackets used on the central, lateral, and cuspid teeth in both the mandibular and maxillary dental arch have a square archwire slot 105. The square archwire slot 105 in these anterior brackets 100 provides for the most accuracy in positioning these anterior teeth 120.

Figure 4B:
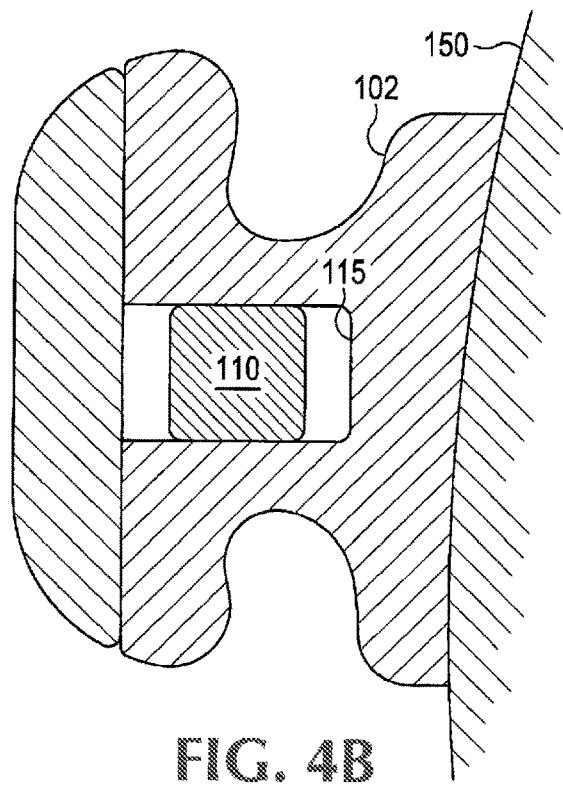
FIG. 4B shows a cross section along line B-B of FIG. 1 using a novel orthodontic system disclosed in the present specification.

FIG. 4B, conversely, shows a dental bracket 102 having a rectangular archwire slot 115 sized to loosely fit around the archwire 110 to be used in the final stage of treatment. The dental bracket 102 having archwire slot 115 is preferably attached to an anterior tooth 150 positioned along the line B-B of FIG. 1. Preferably, brackets 102 having archwire slots 115 of a rectangular cross section are used on bicuspids and molars. Preferably, in some embodiments, the size of the archwire slots 115 of the brackets 102 successively placed on teeth between tooth 120 and tooth 150 varies in some predefined manner from the size and shape depicted in FIG. 4A to the size and shape depicted in FIG. 4B. In this manner, during all stages of treatment, anterior teeth have less freedom of movement than posterior teeth, while at the same time, the teeth in the dental arch as a whole has sufficient freedom of movement.

Those of ordinary skill in the art will appreciate that, in the improved system shown in FIGS. 4A and 4B, the archwire cross section may progress from round at the start of treatment, then through various round and square cross sections over the course of treatment to a final archwire with a square cross section as shown in these two figures. The final square cross section archwire creates forces that are patient friendly and effective for tooth movement. In addition the square cross section of the final archwire provides excellent control of the tooth position.

Those of ordinary skill in the art will also appreciate that other embodiments of the disclosed systems and methods may use other cross sectional shapes than those just described. For example, in some embodiments the dental bracket 100 may have an archwire slot of a rectangular cross section, but smaller than that of the dental bracket 102. Similarly, in some embodiments the dental bracket 102 may have an archwire slot of a square cross section larger than that of the dental bracket 100.

In one preferred embodiment, the final archwire in this system has a labial-lingual dimension of 0.020" and an occlusal-gingival dimension of 0.020" i.e. a 0.020"×0.020" archwire. In other embodiments, the labial-lingual and occlusal-gingival dimensions of the final archwire can range from 0.017"×0.017" square to 0.021"×0.021" square.

The occlusal-gingival dimension of the archwire slot is preferably held constant for all brackets to enhance the accuracy of the torque and tip positioning of all of the teeth in the maxillary and mandibular dental arches. The occlusal-gingival dimension of the archwire slot in all brackets as a percentage of the occlusal-gingival dimension of the archwire in some embodiments is 105% with a range of 102% to 110%. The occlusal-gingival dimension of the archwire slots in the brackets of a system using a final archwire that is 0.020"×0.020" square is 0.021" in such an embodiment, with a range of 0.0204" to 0.022".

Increased freedom of movement is achieved on the bicuspids and the molars by proportionally and progressively increasing the labial-lingual dimension of the archwire slot in the brackets used on these teeth. The labial-lingual dimension of the archwire slot in the brackets is progressively increased as a percentage of the labial-lingual dimension of the archwire from the centrals to the molars in both the maxillary and mandibular dental arches as noted in the following table:

TABLE 1

LABIAL-LINGUAL DIMENSION OF SLOT AS (%) OF ARCHWIRE LABIAL-LINGUAL DIMENSION

| Tooth Position | Preferred Embodiment (%) | Range Minimum (%) | Range Maximum (%) |
| --- | --- | --- | --- |
| Central | 105 | 102 | 110 |
| Lateral | 105 | 102 | 110 |
| Cuspid | 105 | 102 | 110 |
| 1$^{st}$ Bicuspid | 115 | 110 | 125 |
| 2$^{nd}$ Bicuspid | 115 | 110 | 125 |
| 1$^{st}$ Molar | 130 | 120 | 140 |
| 2$^{nd}$ Molar | 130 | 120 | 140 |

The labial-lingual dimension of the archwire slots in the brackets of a system using a final archwire that is 0.020"× 0.020" square are as follows:

TABLE 2

| Tooth Position | Preferred Embodiment (inches) | Range Minimum (inches) | Range Maximum (inches) |
| --- | --- | --- | --- |
| Central | 0.021 | 0.0204 | 0.022 |
| Lateral | 0.021 | 0.0204 | 0.022 |
| Cuspid | 0.021 | 0.0204 | 0.022 |
| 1$^{st}$ Bicuspid | 0.023 | 0.022 | 0.025 |
| 2$^{nd}$ Bicuspid | 0.023 | 0.022 | 0.025 |
| 1$^{st}$ Molar | 0.026 | 0.024 | 0.028 |
| 2$^{nd}$ Molar | 0.026 | 0.024 | 0.028 |

Figure 5A:
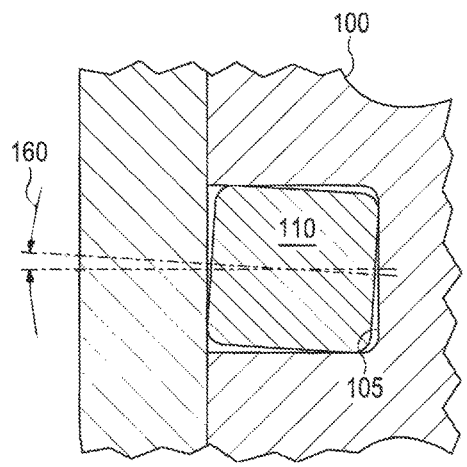
FIGS. 5A-5C show accelerated torque control in the orthodontic system of FIGS. 4A-4B relative to the system of FIGS. 3A-3C.
Figure 5B:
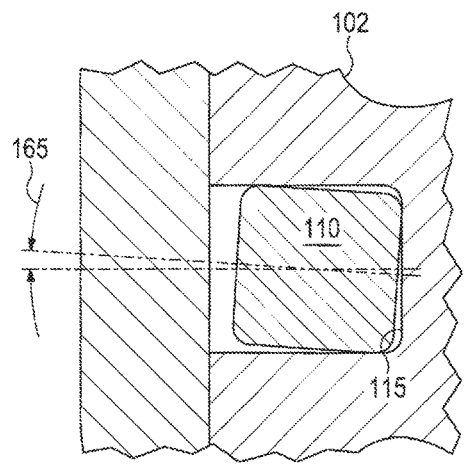
Figure 5C:
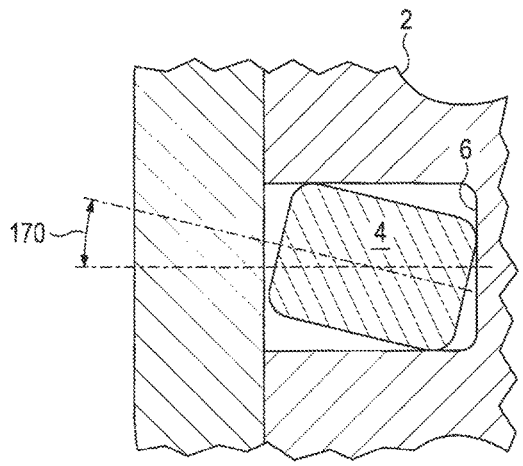

This combination of archwire slot dimensions coupled with a square final archwire, according to the dimensions shown in Tables 1 and 2, provide a system that results in accurate positioning of the anterior teeth while maintaining efficient control of tooth movement for reduced treatment time. Specifically, referring to FIGS. 5A-5C, the archwire slots 105 and 115 provide for much greater control of tooth positioning, earlier in treatment, than do existing systems. FIGS. 5A and 5B illustrate the control over torque provided in the anterior teeth (FIG. 5A) and the posterior teeth (FIG. 5B) using the brackets as shown in FIGS. 4A and 4B during the finishing stages of treatment. As the archwire 110 connecting the brackets 100 and 102 is twisted in the slots 105 and 115, respectively, the corners of the square archwire 110 catch on the sides of the archwire slots at angles of rotation 160 (FIG. 5A) and 165 (FIG. 5B), thereby transmitting forces on the teeth to which the brackets are attached, and consequently inducing the teeth to rotate about an axis oriented in the mesial-distal direction. Notably both the angles 160 and 165 are smaller than the angle 170 shown in FIG. 5C, which shows the result of a rectangular archwire in a rectangular slot. This means that the system of FIGS. 5A and 5B has better control over positioning than does the system of FIG. 5C, at earlier stages of treatment.

Figure 6A:
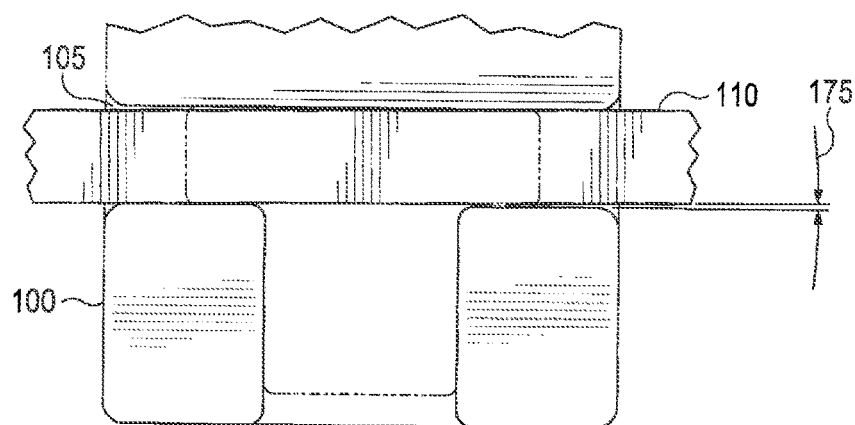
FIGS. 6A-6B show accelerated tip control in the orthodontic system of FIGS. 4A-4B relative to the system of FIGS. 3A-3C.
Figure 6B:
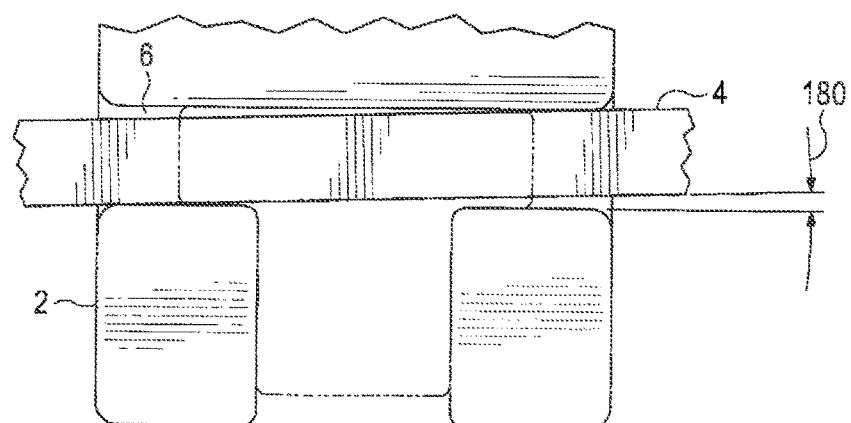

FIGS. 6A and 6B illustrate the same phenomenon with respect to control over "tip." FIG. 6A shows a bracket 100 having an archwire slot 105 through which an archwire is used to position a tooth attached to the bracket. Those of ordinary skill in the art will appreciate that the diagram of FIG. 6A also represents the control over tooth movement provided by bracket 105. Again, the angle 175 is noticeably less than the angle 180 achieved by the prior art system of FIG. 6B.

Figure 7A:
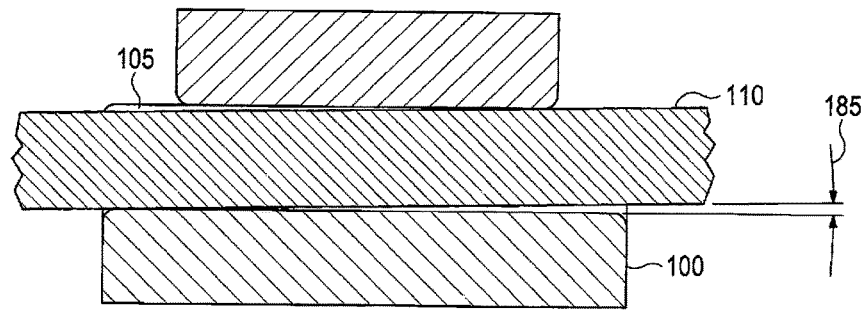
FIGS. 7A-7C show accelerated rotation control in the orthodontic system of FIGS. 4A-4B relative to the system of FIGS. 3A-3C
Figure 7B:
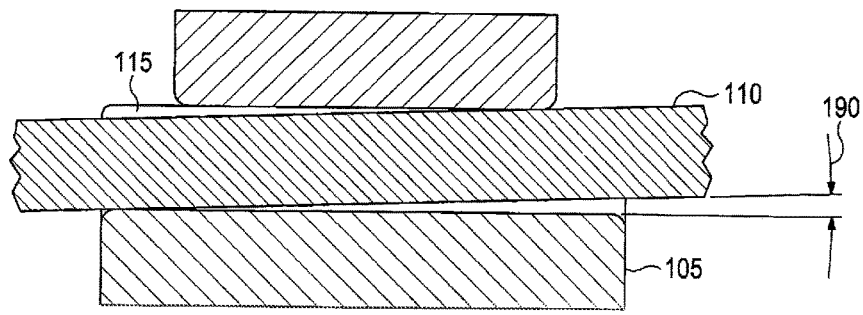
Figure 7C:
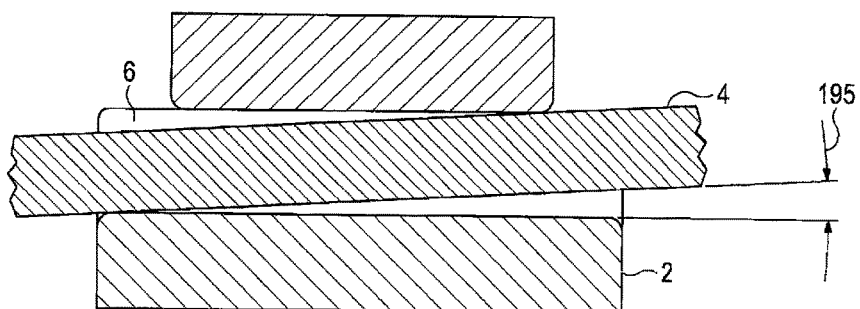

FIGS. 7A-7C illustrate the same phenomenon with respect to control over "rotation." FIG. 7A shows a bracket 100 having an archwire slot 105 through which an archwire is used to position a tooth attached to the bracket. FIG. 7B shows a bracket 105 having an archwire slot 115 through which an archwire is used to position a tooth attached to the bracket. Again, the angles 185 and 190 are each noticeably less than the angle 195 achieved by the prior art system of FIG. 7C.

Using an initial phase of treatment as an illustrative example, where the improved system herein described uses an archwire of 0.014 diameter in archwire slot having measurements shown in Table 2, Table 3 and Table 4 together delineate the improvement in control over torque, tip, and rotation over prior art systems illustrated by FIGS. 5A-7C. In this initial stage of treatment, a round archwire is preferably used, which provides no torque control since the round archwire has no edges to catch on the archwire slot when twisted, but achieves 4.46 degrees of rotation control and 3.83 degrees of tip control. The prior art system in the initial treatment phase, however, though similarly providing no control over torque, can only provide 8.47 degrees of rotation control and 4.29 degrees of tip control. As with control over torque, Table 3 shows that the disclosed system provides greater control over tooth movement at every stage of treatment.

TABLE 3

| | | Disclosed System | | | |
|---|---|---|---|---|---|
| | Phase | Initial | Working | | Finishing & Detailing |
| | X-Section | .014 Rd. | .018 × .018 | .020 × .020 | .020 × .020 |
| | Material | NiTI | NiTi | NiTi | TMA or SS |
| Control | Torque Lock-up | No Control | 14.20 Deg. | 4.18 Deg. | 4.18 Deg. |
| | Rotation Lock-up | 4.46 Deg. | 1.92 Deg. | 0.64 Deg. | 0.64 Deg. |
| | Tip Lock-up | 3.83 Deg. | 1.92 Deg. | 0.55 Deg. | 0.55 Deg. |

TABLE 4

| | | Prior Art System | | | | |
|---|---|---|---|---|---|---|
| | | Phase | | | | |
| | | Initial | | Working | | Finishing & Detailing |
| | X-Section | .014 Rd. | .018 Rd | .014 × .025 | .018 × .025 | .019 × .025 |
| | Material | NiTI | NiTi | NiTi | NiTi | SS |
| Control | Torque Lock-up | No Control | No Control | 28.77 Deg. | 13.78 Deg. | 10.88 Deg. |
| | Rotation Lock-up | 8.47 Deg. | 6.09 Deg. | 1.85 Deg. | 1.85 Deg. | 1.85 Deg. |
| | Tip Lock-up | 4.29 Deg. | 2.15 Deg. | 4.29 Deg. | 2.15 Deg. | 1.62 Deg. |

Although, in theory, the prior art system could be modified to have the degree of control as the presently disclosed system, this would entail narrowing the width of the rectangular archwire slot 6. But in doing so, the force on the patient's teeth caused by the archwire would become excessive and highly uncomfortable to the patient due to the higher moment of inertia of the rectangular archwire as compared to a square archwire. Thus, the system and methods herein disclosed represent a significant improvement over the prior art.

It will be appreciated that the invention is not restricted to the particular embodiment that has been described, and that variations may be made therein without departing from the scope of the invention as defined in the appended claims, as interpreted in accordance with principles of prevailing law, including the doctrine of equivalents or any other principle that enlarges the enforceable scope of a claim beyond its literal scope. Unless the context indicates otherwise, a reference in a claim to the number of instances of an element, be it a reference to one instance or more than one instance, requires at least the stated number of instances of the element but is not intended to exclude from the scope of the claim a structure or method having more instances of that element than stated. The word "comprise" or a derivative thereof, when used in a claim, is used in a nonexclusive sense that is not intended to exclude the presence of other elements or steps in a claimed structure or method.

The invention claimed is:

1. A bracket system for applying a finishing orthodontic treatment, the bracket system comprising:
a first dental bracket having a first archwire slot, the first archwire slot extending downwardly from a top surface of the first dental bracket to a first floor, the first archwire slot having a first depth measured from the top surface in a labial-lingual direction to the first floor and a first width extending across in an occlusal-gingival direction, the first archwire slot sized and dimensioned for receiving an archwire, the first dental bracket further including a first ligating structure extending over the first archwire slot;
a second dental bracket having a second archwire slot, the second archwire slot extending downwardly from a top surface of the second dental bracket to a second floor, the second archwire slot having a second depth measured from the top surface in the labial-lingual direction to the second floor and a second width extending across in an occlusal-gingival direction, the second archwire slot sized and dimensioned for receiving the archwire, the second dental bracket further including a second ligating structure extending over the second archwire slot, wherein the first depth of the first archwire slot is shallower relative to the top surface of the first dental bracket as compared to the second depth of the second archwire slot relative to the top surface of the second bracket;
a third dental bracket having a third archwire slot extending downwardly from a top surface of the third dental bracket to a third floor, the third archwire slot having a third depth measured from the top surface in a labial-lingual direction to the third floor and a third width extending across in an occlusal-gingival direction, the third archwire slot sized and dimensioned for receiving the archwire, wherein the third archwire slot has a different size than that of the first archwire slot and a different size than that of the second archwire slot, and
a square-shaped finishing archwire extending through each of the first archwire slot, the second archwire slot, and the third archwire slot, wherein the first depth in the labial-lingual direction of the first archwire slot ranges between 102% and 110% of the corresponding labial-lingual dimension of the square-shaped finishing archwire, and wherein the second depth in the labial-lingual direction of the second archwire slot ranges between 110% and 125% of the corresponding labial-lingual dimension of the square-shaped finishing archwire, and wherein the third depth in the labial-lingual direction of the third archwire slot ranges between 120% and 140% of the corresponding labial-lingual dimension of the square-shaped finishing archwire.

2. The system of claim 1 wherein the first archwire slot has a different cross-sectional shape than that of the second archwire slot.

3. The system of claim 1 wherein the first dental bracket is affixable to an anterior tooth and the second dental bracket is affixable to a posterior tooth.

4. The system of claim 1 wherein the respective first depth, second depth, and third depth of the first, second, and third archwire slots increases in the distal direction of the arch relative to the dental midline.

5. The system of claim 4, wherein the first width, second width, and third width of the respective first archwire slot, second archwire slot, and third archwire slot in the occlusal-gingival direction are substantially the same.

6. The system of claim 1, wherein a first portion of a bottom surface of the square-shaped archwire is seated against and contacts the first floor of the first archwire slot, and wherein a second portion of the bottom surface of the square-shaped archwire is spaced apart and offset from the first floor of the first archwire slot.

7. The system of claim 6, wherein a third portion of an upper surface of the square-shaped archwire contacts the first ligating structure, and wherein a fourth portion of the upper surface of the square-shaped archwire is spaced apart and offset from the first ligating structure.

8. The system of claim 6, wherein a third portion of the bottom surface of the square-shaped archwire is seated against and contacts the second floor of the second archwire slot, and wherein a second portion of the bottom surface of the square-shaped archwire is spaced apart and offset from the second floor of the second archwire slot.

9. A method for applying a finishing orthodontic treatment, the method comprising:
   affixing a first dental bracket to a first tooth, the first dental bracket having a first archwire slot, the first archwire slot extending downwardly from a top surface of the first dental bracket to a first floor, the first archwire slot having a first depth measured from the top surface in a labial-lingual direction to the first floor and a first width extending across in an occlusal-gingival direction, the first archwire slot sized and dimensioned for receiving an archwire, the first dental bracket further including a first ligating structure extending over the first archwire slot;
   affixing a second dental bracket to a second tooth, the second dental bracket having a second archwire slot, the second archwire slot extending downwardly from a top surface of the second dental bracket to a second floor, the second archwire slot having a second depth measured from the top surface in the labial-lingual direction to the second floor and a second width extending across in an occlusal-gingival direction, the second archwire slot sized and dimensioned for receiving the archwire, the second dental bracket further including a second ligating structure extending over the second archwire slot, wherein the first depth of the first archwire slot is shallower relative to the top surface of the first dental bracket as compared to the second depth of the second archwire slot relative to the top surface of the second bracket;
   affixing a third dental bracket to a third tooth, the third dental bracket having a third archwire slot extending downwardly from a top surface of the third dental bracket to a third floor, the third archwire slot having a third depth measured from the top surface in a labial-lingual direction to the third floor and a third width extending across in an occlusal-gingival direction, the third archwire slot sized and dimensioned for receiving the archwire, wherein the third archwire slot has a different size than that of the first archwire slot and a different size than that of the second archwire slot;
   during a first phase of treatment, positioning a round-shaped archwire through the first dental bracket, the second dental bracket, and the third dental bracket, the round-shaped archwire extending through the first archwire slot, the second archwire slot, and the third archwire slot of the respective first, second, and third dental brackets;
   after the first phase of treatment, removing the round-shaped archwire from the first, second, and third dental brackets, and
   during a final phase of treatment, positioning a square-shaped finishing archwire through each of the first archwire slot, the second archwire slot, and the third archwire slot of the respective first, second, and third dental brackets, wherein the first depth in the labial-lingual direction of the first archwire slot ranges between 102% and 110% of the corresponding labial-lingual dimension of the square-shaped finishing archwire, and wherein the second depth in the labial-lingual direction of the second archwire slot ranges between 110% and 125% of the corresponding labial-lingual dimension of the square-shaped finishing archwire, and wherein the third depth in the labial-lingual direction of the third archwire slot ranges between 120% and 140% of the corresponding labial-lingual dimension of the square-shaped finishing archwire.

10. The method of claim 9 wherein the first archwire slot has a square cross section and the second archwire slot has a rectangular cross section.

11. The method of claim 9 wherein the first dental bracket is affixable to an anterior tooth and the second dental bracket is affixable to a posterior tooth.

12. The method of claim 9 wherein the first width and second width of the respective first archwire slot and second archwire slot in the occlusal-gingival direction are substantially the same.

13. The method of claim 9, wherein a first portion of a bottom surface of the square-shaped archwire is seated against and contacts the first floor of the first archwire slot, and wherein a second portion of the bottom surface of the square-shaped archwire is spaced apart and offset from the first floor of the first archwire slot.

14. The method of claim 13, wherein a third portion of an upper surface of the square-shaped archwire contacts the first ligating structure, and wherein a fourth portion of the upper surface of the square-shaped archwire is spaced apart and offset from the first ligating structure.

15. The method of claim 13, wherein a third portion of the bottom surface of the square-shaped archwire is seated against and contacts the second floor of the second archwire slot, and wherein a second portion of the bottom surface of the square-shaped archwire is spaced apart and offset from the first floor of the first archwire slot.

* * * * *

UNITED STATES PATENT AND TRADEMARK OFFICE
CERTIFICATE OF CORRECTION

PATENT NO. : 10,357,337 B2
APPLICATION NO. : 15/601646
DATED : July 23, 2019
INVENTOR(S) : Thomas Pitts and Alberto Ruiz-Vela It is certified that error appears in the above-identified patent and that said Letters Patent is hereby corrected as shown below:

In the Claims

Column 8:
Line 35, after "second" insert --dental--.
Line 46, change "slot," to --slot;--.
Line 62, change "claim 1 wherein" to --claim 1, wherein--.
Line 65, change "claim 1 wherein" to --claim 1, wherein--.

Column 9:
Line 1, change "claim 1 wherein" to --claim 1, wherein--.

Column 10:
Line 15, change "brackets," to --brackets;--.
Line 32, change "claim 9 wherein" to --claim 9, wherein--.
Line 35, change "claim 9 wherein" to --claim 9, wherein--.
Line 38, change "claim 9 wherein" to --claim 9, wherein--.

Signed and Sealed this
Eleventh Day of April, 2023

Katherine Kelly Vidal
*Director of the United States Patent and Trademark Office*